(12) United States Patent
Ganta et al.

(10) Patent No.: US 7,914,632 B2
(45) Date of Patent: Mar. 29, 2011

(54) GAS GENERANT COMPOSITIONS

(75) Inventors: Sudhakar R. Ganta, Troy, MI (US);
Graylon K. Williams, Warren, MI (US);
Cory G. Miller, Rochester, MI (US)

(73) Assignee: TK Holdings, Inc., Armada, MI (US)

( * ) Notice: Subject to any disclaimer, the term of this patent is extended or adjusted under 35 U.S.C. 154(b) by 995 days.

(21) Appl. No.: 11/800,918

(22) Filed: May 7, 2007

(65) Prior Publication Data
US 2010/0258220 A1 Oct. 14, 2010

Related U.S. Application Data

(60) Provisional application No. 60/798,206, filed on May 5, 2006.

(51) Int. Cl.
*C06B 31/00* (2006.01)
*C06B 31/02* (2006.01)
*C06B 29/00* (2006.01)
*C06B 29/02* (2006.01)
*D03D 23/00* (2006.01)
*D03D 43/00* (2006.01)

(52) U.S. Cl. ............... 149/45; 149/61; 149/75; 149/77; 149/109.2; 149/109.4

(58) Field of Classification Search .............. 149/45, 149/61, 75, 77, 109.2, 109.4
See application file for complete search history.

(56) References Cited

U.S. PATENT DOCUMENTS

| | | | |
|---|---|---|---|
| 3,719,604 A | 3/1973 | Prior et al. | 252/186 |
| 3,954,528 A | 5/1976 | Chang et al. | 149/19.4 |
| 4,142,029 A | 2/1979 | Illy | 521/95 |
| 4,636,457 A | 1/1987 | Valbusa et al. | 430/267 |
| 4,921,965 A | 5/1990 | Rothgery et al. | 548/251 |
| 4,988,811 A | 1/1991 | Valbusa et al. | 544/207 |
| 5,773,754 A | 6/1998 | Yamato | 149/36 |
| 6,074,502 A | 6/2000 | Burns et al. | 149/36 |
| 6,552,051 B2 | 4/2003 | Bottaro et al. | 514/359 |
| 6,590,118 B1 | 7/2003 | Kristiansen et al. | 558/416 |
| 7,237,801 B2 | 7/2007 | Quioc et al. | 280/736 |

(Continued)

FOREIGN PATENT DOCUMENTS
WO  WO 2006/050442  5/2006

OTHER PUBLICATIONS

Fleming, et al. Reactions of bis(tetrazole)phenylenes, Surprising formation of vinyl compounds from alkyl halides. Tetrahedron. May 2005, vol. 61(29), pp. 7002-7011, especially p. 7003.

(Continued)

*Primary Examiner* — James E McDonough
(74) *Attorney, Agent, or Firm* — L.C. Begin & Associates, PLLC.

(57) ABSTRACT

A novel compound, used for example, as a gas generating fuel, is methoxy carbonyl-5 amino tetrazole. A method of making the compound is also provided. A gas generating composition, containing the novel compound as a fuel, and an oxidizer is also provided. The novel compound may be contained within a gas generant composition 12, within a gas generator 10. The gas generator 10 may be contained within a gas generating system 200 such as an airbag inflator 10 or seat belt assembly 150, or more broadly within a vehicle occupant protection system 180.

13 Claims, 1 Drawing Sheet

U.S. PATENT DOCUMENTS

| | | | |
|---|---|---|---|
| 7,692,024 B2 | 4/2010 | Ganta et al. | 548/250 |
| 2003/0145923 A1 | 8/2003 | Redecker et al. | 149/36 |
| 2004/0053908 A1 | 3/2004 | Funahashi et al. | 514/183 |
| 2004/0226639 A1 | 11/2004 | Redecker et al. | 149/45 |
| 2005/0082804 A1* | 4/2005 | Khandhadia | 280/736 |
| 2005/0230017 A1* | 10/2005 | Williams et al. | 149/46 |
| 2005/0257866 A1* | 11/2005 | Williams et al. | 149/36 |
| 2005/0263224 A1 | 12/2005 | Wu et al. | 149/46 |
| 2006/0005734 A1 | 1/2006 | McCormick | 102/530 |
| 2006/0016529 A1 | 1/2006 | Barnes et al. | 149/45 |
| 2007/0102076 A1 | 5/2007 | Redecker et al. | 149/36 |
| 2008/0110536 A1 | 5/2008 | Ganta et al. | 149/45 |
| 2008/0154044 A1 | 6/2008 | Ganta et al. | 548/251 |
| 2008/0169051 A1 | 7/2008 | Ganta et al. | 149/74 |

OTHER PUBLICATIONS

Demko, et al. Preparation of 5-Substituted 1H-Tetrazoles from Nitriles in Water. J. Org. Chem. Jun. 2001, vol. 66(24), pp. 7945-7950, especially p. 7946.
PCT Written Opinion, PCT/US07/11107, Dated Jun. 3, 2008.
PCT Written Opinion, PCT/US07/11051, Dated Nov. 27, 2007.
PCT Written Opinion, PCT/US07/11108, Dated Apr. 15, 2008.
PCT Written Opinion, PCT/US07/11109, Dated Apr. 24, 2008.
PCT Written Opinion, PCT/US07/21143, Dated Aug. 1, 2008.

* cited by examiner

GAS GENERANT COMPOSITIONS

CROSS-REFERENCE TO RELATED APPLICATIONS

This application claims the benefit of U.S. Provisional Application Ser. No. 60/798,206 filed on May 5, 2006.

TECHNICAL FIELD

The present invention relates generally to gas generating systems, and to gas generating compositions employed in gas generator devices for automotive restraint systems, for example.

BACKGROUND OF THE INVENTION

The present invention relates to gas generant compositions that upon combustion produce a relatively smaller amount of solids and a relatively abundant amount of gas. It is an ongoing challenge to reduce the amount of solids and increase the amount of gas thereby decreasing the filtration requirements for an inflator. As a result, the filter may be either reduced in size or eliminated altogether thereby reducing the weight and/or size of the inflator. Additionally, reduction of combustion solids provides relatively greater amounts of gaseous products per gram or unit of gas generating composition. Accordingly, less gas generant is required when greater mols of gas are produced per gram of gas generant. The result is typically a smaller and less expensive inflator due to reduced manufacturing complexity.

Yet another concern is that the compositions must exhibit burn rates that are satisfactory with regard to use in vehicle occupant protection systems. In particular, compositions containing phase stabilized ammonium nitrate may exhibit relatively lower burn rates requiring various measures to improve the burn rate. Accordingly, the development of energetic fuels is one ongoing research emphasis whereby the less aggressive burn characteristics of preferred oxidizers such as phase stabilized ammonium nitrate are accommodated and compensated.

SUMMARY OF THE INVENTION

The above-referenced concerns are resolved by gas generators or gas generating systems containing a novel fuel constituent, methoxy carbonyl-5 amino tetrazole, within novel gas generant compositions. It will be appreciated that the novel compound formed in accordance with the present invention may have applications other than as a gas generant constituent.

An optional second fuel may be selected from tetrazoles and salts thereof, triazoles and salts thereof, azoles and salts thereof, guanidines and salts thereof, guanidine derivatives, amides, and mixtures thereof. An oxidizer is selected from metal and nonmetal nitrates, nitrites, chlorates, perchlorates, oxides, other known oxidizers, and mixtures thereof.

In further accordance with the present invention, a gas generator or gas generating system, and a vehicle occupant protection system incorporating the gas generant composition are also included.

DETAILED DESCRIPTION OF THE INVENTION

Figure 1:
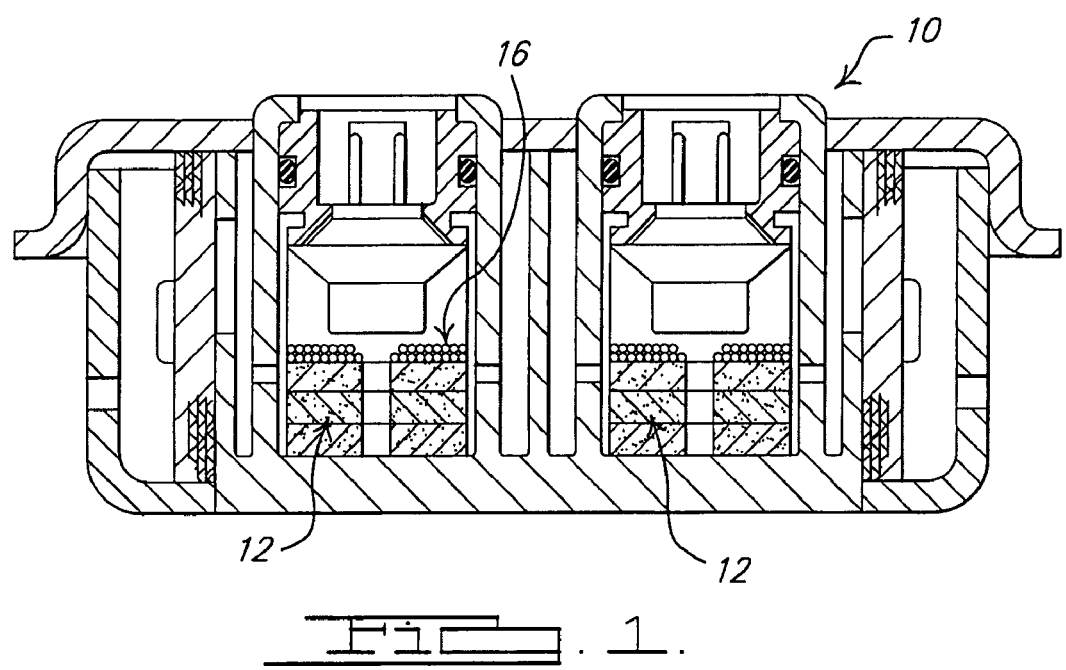
FIG. 1 is a cross-sectional side view showing the general structure of an inflator in accordance with the present invention.

A first aspect of the present invention provides a novel method of forming a nitrogen-containing compound, useful as a fuel within a gas generant system, for example. The method may be described by the following steps:

1. Providing a solution of 5-amino tetrazole and triethyl amine in acetonitrile, wherein 5-amino tetrazole and triethyl amine are provided in roughly equimolar amounts, and acetonitrile is provided in an amount sufficient to solublize the reactants of this method, at a temperature of 0 C to room temperature.
2. Adding methyl chloroformate in a substantially equimolar amount as the triethyl amine, to a cooled solution.
3. Stir the mixture and slowly bring to room temperature.
4. Reflux for about two hours to form a reactant solid in a closed container.
5. Cool to room temperature.
6. Remove the remaining solvent, preferably under vacuum conditions, wherein residue remains.
7. Wash the residue with dilute 3N hydrochloric acid to yield a white-colored solid.

The reaction given below illustrates the formation of the fuel.

I) (1H-Tetrazol-5-yl)-carbamic acid methyl ester

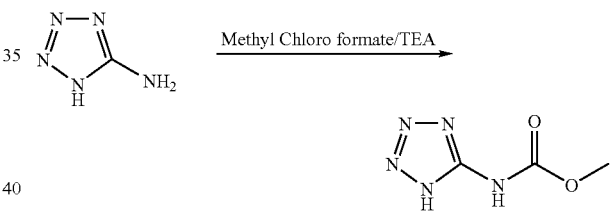

Experimental Procedure for the synthesis of Methoxy carbonyl-5 Amino Tetrazole.:

To a solution of 5-Amino tetrazole (10.00 g, 117.56 mmol)/Triethyl amine (16.48 ml, 118.739 mmol) in acetonitrile was added Methyl chloroformate (9.1375 ml, 118.739 mmol) at 0° C. The reaction mixture was slowly brought to room temperature and stirred for about 30 minutes. After about 30 minutes the reaction warmed and was refluxed for about 2 hrs. The reaction was then cooled to room temperature and the solvent was removed under reduced pressure, leaving a residue. The residue was washed with dilyte HCl to yield a white-colored solid. The solid was then dried at 105 C for about 6 hrs, resulting in a 92% yield.

Infrared (IR) evaluations indicated 3246 cm$^{-1}$(N-H stretching), 1728 cm$^{-1}$ (carbamate), 1640, 1525 cm$^{-1}$ (tetrazole), 1434, 1226 cm-1, thereby confirming the structure of the product. Differential Scanning Calorimetry (DSC) evaluation resulted in an endotherm at 236° C.

The reaction product exhibited relatively high energy and when combined with oxidizers as described below, also exhibited good burn rates in excess of 0.4 inches per second, when evaluated as known in the art.

Theoretical Calculation:

With a fuel/oxidizer ratio of 24/76, that is THIS FUEL/PSAN in wt %, then the propellant oxygen balance equals −0.76. This oxygen balance results in a 96.5% gas yield and produces 4.04 moles of gas per 100 gm of propellant.

Each fuel is nitrogen-rich, thereby maximizing the nonmetal constituents of the total gas generant composition.

The fuel is provided at about 5-50 wt % and more preferably at about 15-30 wt %, of the gas generant composition.

Optional secondary fuels include tetrazoles such as 5-aminotetrazole; metal salts of azoles such as potassium 5-aminotetrazole; nonmetal salts of azoles such as diammonium salt of 5,5'-bis-1H-tetrazole: nitrate salts of azoles such as 5-aminotetrazole; nitramine derivatives of azoles such as 5-aminotetrazole; metal salts of nitramine derivatives of azoles such as dipotassium 5-aminotetrazole; metal salts of nitramine derivatives of azoles such as dipotassium 5-aminotetrazole; nonmetal salts of nitramine derivatives of azoles such as monoammonium 5-aminotetrazole and; guanidiness such as dicyandiamide; salts of guanidines such as guanidine nitrate; nitro derivatives of guanidines such as nitroguanidine; azoamides such as azodicarbonamide; nitrate salts of azoamides such as azodicarbonamidine dinitrate; and mixtures thereof. The secondary fuel can be used within this system as co-fuels to the primary fuel. If used, the secondary fuel when combined with the primary fuel constitutes about 5-50 wt % of the gas generant composition. By itself, the secondary fuel constitutes 0-45 wt %, and more preferably about 15-30 wt % when used.

An oxidizer component is selected from at least one exemplary oxidizer selected from basic metal nitrates, and, metal and nonmetal nitrates, chlorates, perchlorates, nitrites, oxides, and peroxides such as basic copper (II) nitrate, strontium nitrate, potassium nitrate, potassium nitrite, iron oxide, and copper oxide. Other oxidizers as recognized by one of ordinary skill in the art may also be employed. The oxidizer is generally provided at about 50-95 wt % of the gas generant composition.

Processing aids such as fumed silica, boron nitride, and graphite may also be employed. Accordingly, the gas generant may be safely compressed into tablets, or slugged and then granulated. The processing aid is generally provided at about 0-15 wt %, and more preferably at about 0-5 wt %.

Slag formers may also be provided and are selected from silicon compounds such as elemental silicone; silicon dioxide; silicones such as polydimethylsiloxane; silicates such as potassium silicates; natural minerals such as talc and clay, and other known slag formers. The slag former is typically provided at about 0-10 wt %, and more preferably at about 0-5 wt %.

The compositions of the present invention are formed from constituents as provided by known suppliers such as Aldrich or Fisher Chemical companies. The compositions may be provided in granulated form and dry-mixed and compacted in a known manner, or otherwise mixed as known in the art. The compositions may be employed in gas generators typically found in airbag devices or occupant protection systems, or in safety belt devices, or in gas generating systems such as a vehicle occupant protection system, all manufactured as known in the art, or as appreciated by one of ordinary skill.

As shown in FIG. 1, an exemplary inflator or gas generating system 10 incorporates a dual chamber design to tailor containing a primary gas generating composition 12 formed as described herein, may be manufactured as known in the art. U.S. Pat. Nos. 6,422,601, 6,805,377, 6,659,500, 6,749,219, and 6,752,421 exemplify typical airbag inflator designs and are each incorporated herein by reference in their entirety.

Figure 2:
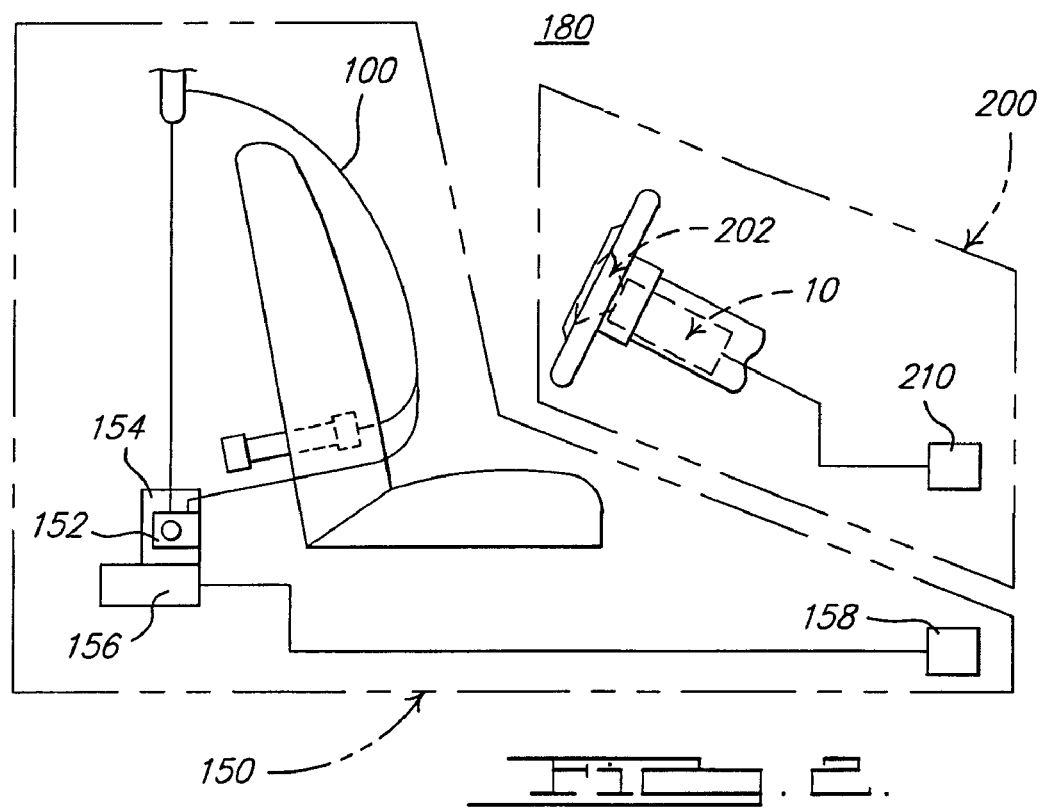
FIG. 2 is a schematic representation of an exemplary vehicle occupant restraint system containing a gas generant composition in accordance with the present invention.

Referring now to FIG. 2, the exemplary inflator or gas generating system 10 described above may also be incorporated into an airbag system 200. Airbag system 200 includes at least one airbag 202 and an inflator 10 containing a gas generant composition 12 in accordance with the present invention, coupled to airbag 202 so as to enable fluid communication with an interior of the airbag. Airbag system 200 may also include (or be in communication with) a crash event sensor 210. Crash event sensor 210 includes a known crash sensor algorithm that signals actuation of airbag system 200 via, for example, activation of airbag inflator 10 in the event of a collision.

Referring again to FIG. 2, airbag system 200 may also be incorporated into a broader, more comprehensive vehicle occupant restraint system 180 including additional elements such as a safety belt assembly 150. FIG. 2 shows a schematic diagram of one exemplary embodiment of such a restraint system. Safety belt assembly 150 includes a safety belt housing 152 and a safety belt 100 extending from housing 152. A safety belt retractor mechanism 154 (for example, a spring-loaded mechanism) may be coupled to an end portion of the belt. In addition, a safety belt pretensioner 156 containing gas generating/auto ignition composition 12 may be coupled to belt retractor mechanism 154 to actuate the retractor mechanism in the event of a collision. Typical seat belt retractor mechanisms which may be used in conjunction with the safety belt embodiments of the present invention are described in U.S. Pat. Nos. 5,743,480, 5,553,803, 5,667,161, 5,451,008, 4,558,832 and 4,597,546, incorporated herein by reference. Illustrative examples of typical pretensioners with which the safety belt embodiments of the present invention may be combined are described in U.S. Pat. Nos. 6,505,790 and 6,419,177, incorporated herein by reference.

Safety belt assembly 150 may also include (or be in communication with) a crash event sensor 158 (for example, an inertia sensor or an accelerometer) including a known crash sensor algorithm that signals actuation of belt pretensioner 156 via, for example, activation of a pyrotechnic igniter (not shown) incorporated into the pretensioner. U.S. Pat. Nos. 6,505,790 and 6,419,177, previously incorporated herein by reference, provide illustrative examples of pretensioners actuated in such a manner.

It should be appreciated that safety belt assembly 150, airbag system 200, and more broadly, vehicle occupant protection system 180 exemplify but do not limit gas generating systems contemplated in accordance with the present invention.

It should further be understood that the preceding is merely a detailed description of various embodiments of this invention and that numerous changes to the disclosed embodiments can be made in accordance with the disclosure herein without departing from the scope of the invention. The preceding description, therefore, is not meant to limit the scope of the invention. Rather, the scope of the invention is to be determined only by the appended claims and their equivalents.

What is claimed is:
1. A compound defined as having the structural formula of:

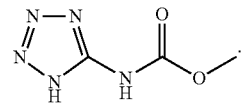

2. A composition comprising:
Methoxy carbonyl-5 amino tetrazole as a first fuel, said fuel provided at about 5-50 weight percent;

an oxidizer selected from basic metal nitrates, and, metal and nonmetal nitrates, chlorates, perchlorates, nitrites, oxides, and peroxides, said oxidizer provided at about 50-95 weight percent.

3. The composition of claim 2 further comprising:
a second fuel selected from carboxylic acids; amino acids; tetrazoles; triazoles; guanidines; azoamides; metal and nonmetal salts thereof; and mixtures thereof, said second fuel provided at about 0.1-45 weight percent.

4. A gas generating system containing the compound of claim 1.

5. A vehicle occupant protection system containing the compound 1.

6. A gas generating system containing the composition of claim 2.

7. A vehicle occupant protection system containing the composition of claim 2.

8. A composition containing the compound of claim 1.

9. A method of forming a compound comprising the steps of:
providing a solution of 5-amino tetrazole and triethyl amine in acetonitrile, wherein 5-amino tetrazole and triethyl amine are provided in roughly equimolar amounts, and acetonitrile is provided in an amount sufficient to solubilize the reactants of this method;
adding methyl chloroformate in a substantially equimolar amount as the triethyl amine, to a cooled solution;
stir the mixture and slowly bring to room temperature;
reflux the solution to form a reactant solid; and
remove excess solvent.

10. A compound formed by a method comprising the steps of:
providing a solution of 5-amino tetrazole and triethyl amine in acetonitrile, wherein 5-amino tetrazole and triethyl amine are provided in roughly equimolar amounts, and acetonitrile is provided in an amount sufficient to solubilize the reactants of this method;
adding methyl chloroformate in a substantially equimolar amount as the triethyl amine, to a cooled solution;
stir the mixture and slowly bring to room temperature;
reflux the solution to form a reactant solid; and
remove excess solvent.

11. A gas generant composition containing a compound formed by a method comprising the steps of:
providing a solution of 5-amino tetrazole and triethyl amine in acetonitrile, wherein 5-amino tetrazole and triethyl amine are provided in roughly equimolar amounts, and acetonitrile is provided in an amount sufficient to solubilize the reactants of this method;
adding methyl chloroformate in a substantially equimolar amount as the triethyl amine, to a cooled solution;
stir the mixture and slowly bring to room temperature;
reflux the solution to form a reactant solid; and
remove excess solvent.

12. A gas generating system containing the compound formed by the method of claim 9.

13. A vehicle occupant protection system containing the compound formed by the method of claim 9.

* * * * *

UNITED STATES PATENT AND TRADEMARK OFFICE
CERTIFICATE OF CORRECTION

| | | |
|---|---|---|
| PATENT NO. | : 7,914,632 B2 | Page 1 of 1 |
| APPLICATION NO. | : 11/800918 | |
| DATED | : March 29, 2011 | |
| INVENTOR(S) | : Ganta et al. | |

It is certified that error appears in the above-identified patent and that said Letters Patent is hereby corrected as shown below:

Column 2, Line 58, Please delete "cm-1" and insert -- cm --.

Signed and Sealed this
Fourteenth Day of June, 2011

David J. Kappos
*Director of the United States Patent and Trademark Office*